(12) United States Patent
Lin et al.

(10) Patent No.: US 8,911,329 B2
(45) Date of Patent: Dec. 16, 2014

(54) REAL-TIME EXERCISE COACHING SYSTEM

(71) Applicant: Advanced Mediwatch Co., Ltd., Taipei (TW)

(72) Inventors: Sung-Lien Lin, New Taipei (TW); Tung-Hung Lu, Taipei (TW); Shang-Ting Lin, Taipei (TW)

(73) Assignee: Advanced Mediwatch Co., Ltd., Taipei (TW)

( * ) Notice: Subject to any disclaimer, the term of this patent is extended or adjusted under 35 U.S.C. 154(b) by 217 days.

(21) Appl. No.: 13/734,465

(22) Filed: Jan. 4, 2013

(65) Prior Publication Data
US 2013/0178335 A1 Jul. 11, 2013

(30) Foreign Application Priority Data

Jan. 6, 2012 (TW) .............................. 101100721 A

(51) Int. Cl.
*A63B 24/00* (2006.01)
(52) U.S. Cl.
USPC ................... 482/8; 482/1; 482/901; 600/300; 600/301
(58) Field of Classification Search
USPC ................... 482/1–9, 900–902; 600/300, 301; 700/91
See application file for complete search history.

(56) References Cited

U.S. PATENT DOCUMENTS

| 7,789,802 | B2 | 9/2010 | Lee et al. | |
| 7,828,697 | B1 | 11/2010 | Oberrieder et al. | |
| 8,033,959 | B2 | 10/2011 | Oleson et al. | |
| 8,157,731 | B2 * | 4/2012 | Teller et al. | 600/301 |
| 8,398,546 | B2 * | 3/2013 | Pacione et al. | 600/300 |
| 2014/0094707 | A1 * | 4/2014 | Farringdon et al. | 600/509 |
| 2014/0249661 | A1 * | 9/2014 | Dibenedetto et al. | 700/91 |

* cited by examiner

*Primary Examiner* — Glenn Richman
(74) *Attorney, Agent, or Firm* — WPAT, P.C.; Anthony King

(57) ABSTRACT

The invention provides a real-time exercise coaching system on the basis of that the whole exercise course could be subdivided into 4 basic components: sprint (anaerobic or speeding), aerobic endurance (balancing aerobic endurance), compensating (compensating $O_2$ debt), and dynamic recovery. The real-time exercise coaching system of the invention enables a user to realize his/her current physiological state and change of fitness condition and then the user can further decide which action (sprint, aerobic endurance, and dynamic recovery) is to be taken next. The system of the invention instantly and continuously provides information that assesses a user's current physiological state during exercising in view of the exercise situations and the environmental conditions (such as temperature, humidity, altitude and air quality).

26 Claims, 2 Drawing Sheets

REAL-TIME EXERCISE COACHING SYSTEM

FIELD OF THE INVENTION

The invention relates generally to fitness monitoring systems. In particular, the invention relates to a real-time exercise coaching system.

BACKGROUND OF THE INVENTION

Medical data show that a regular exercise leads to a healthier life. Exercise is important to maintaining a healthy lifestyle and an individual's wellbeing. Accordingly, many individuals want to participate in exercise programs. The fitness of the heart is the key to one's aerobic endurance—cardiovascular respiratory endurance. For health and racing reasons, aerobic endurance is a point of focus for almost any runner. Aerobic and anaerobic capacities reflect the condition of a subject's aerobic and anaerobic metabolisms, respectively. Aerobic metabolism refers to the body's method of producing energy by a process requiring oxygen. Whenever the available amount of oxygen-based energy fails to meet the demand, an anaerobic state occurs where energy is produced by a process that does not require oxygen, but may result in an oxygen debt. Thus, aerobic and anaerobic metabolisms are related but are separate functions.

It is of value to distinguish the aerobic metabolism energy sources from anaerobic metabolism energy sources. Muscles contract from the phosphorylation of adenine triphosphate (ATP). Metabolic energy sources replenish the ATP when sustained or repeated muscle contractions occur. Aerobic oxidative phosphorylation provides ATP at a steady rate until the energy reserves of glycogen or fatty acids have been depleted. At this point, or just prior to this point, anaerobic metabolism begins. Also, anaerobic metabolism is also called upon when a higher level of mechanical work is required. The anaerobic metabolism sources of ATP are less efficient, require more caloric energy to produce ATP, deplete sooner, and produce an oxygen debt.

Physical exercise is an important activity that many individuals undertake to maintain their physical fitness. It has been shown, for example, that physical fitness contributes positively toward maintaining healthy body weight; building and maintaining healthy bone density, muscle strength, and joint mobility; promoting physiological well-being; reducing surgical risks; and strengthening the immune system. Athletes and fitness buffs often monitor and record certain performance values while they train and exercise. For example, runners, bikers, and other athletes often track and record their distance, speed, pace, heart rate, and/or burned calories during a workout so that they can compare these performance values to benchmark values or to values from previous workouts. Historically, these performance values have been monitored and recorded with various different stand-alone components including stop watches, pedometers, heart rate monitors, and calorie calculators or charts. Those skilled in the art will appreciate the fact that the use of all these different components is time-consuming, cumbersome, and often inaccurate.

To alleviate some of these problems, portable personal training devices have been developed to simplify and improve exercise monitoring. Information about the individual's progress toward achieving their goals may be collected by using sensors that measure various physical and/or physiological parameters associated with the individual's physical activity. U.S. Pat. No. 7,828,697 relates to a portable personal training device including a location determining component operable to determine a geographic location of the device, where a housing having a first portion and a second portion coupled to the first portion at an angle, and a strap operable to secure the housing to a user's wrist such that the first portion is operable to be positioned on a top of the wrist and the second portion is operable to be positioned offset from the top of the wrist. Such a configuration facilitates both the wearing and the operation of the device. U.S. Pat. No. 7,789,802 provides a physical training device using GPS data to assist a user in reaching the user's performance goals and completing training sessions by tracking the user's performance, by communicating progress including progress relative to user-defined goals, by communicating navigation directions and waypoints, and by storing and analyzing training session statistics. U.S. Pat. No. 8,033,959 further provides a portable fitness monitoring system that includes: a portable fitness monitoring device; a sensor that communicates with the portable fitness monitoring device to sense the performance parameters during a physical activity conducted by the user and to communicate the performance parameter data to the dedicated portable fitness monitoring device; a music device directly coupled to the portable fitness monitoring device; and an audio output device directly coupled to the portable fitness monitoring device, wherein music is transmitted from the portable music device to the audio output device through the portable fitness monitoring device.

Although the above portable fitness monitoring devices have been provided, they only rely on heart rate as the main parameter without immediate analysis; meanwhile some use a fixed calculation table to cover all individuals but neglect health and environmental conditions. These devices fail to take personally physiological state, exercise types (such as aerobic and anaerobic exercises) and workout environmental conditions (such as temperature, humidity, altitude and air quality) into consideration. In view of the fact that physiological states, exercise types and environments can also contribute to a variation in heart rate, these devices overly simplify the fitness assessment or such an analysis is produced after the end of exercise. Thus a user cannot instantly and continuously realize the changes to his/her physical conditions and can only evaluate his/her performances based on his/her heart rate during an exercise. Therefore, there is still a need to develop an exercise status display and a coaching system that is capable of providing instant physical information so that a user can realize his/her current physical state and further decide which action (such as sprint, aerobic endurance or dynamic recovery) is to be taken next.

SUMMARY OF THE INVENTION

The invention provides a real-time exercise coaching system comprising: (a) a heart rate (HR) module to acquire heart rate parameters; (b) a process unit module to retrieve the parameters from the HR module to obtain a HR reading and/or heart rate intensity (HR intensity) and determine a real-time workload status: a sprint or compensating state if the HR reading or HR intensity significantly increases; an aerobic endurance state if the increased HR intensity is fixed within a zone wherein the HR intensity fluctuates between a range about +/−1 to about +/−20% of the average HR intensity of this state; and a dynamic recovery state if the HR intensity decreases about 1% to about 20% than an average HR intensity during the aerobic endurance state for a time period that is longer than that of the sprint or compensating state; and (c) an output module to display the real-time workload status including the sprint, the compensating, the aerobic endurance or the dynamic recovery statuses.

The invention also provides a method of real-time coaching exercise, comprising (a) acquiring HR parameters; (b) retrieving the HR parameters from the HR module to obtain a HR reading and/or heart rate intensity (HR intensity) and determining a real-time workload status: a sprint or compensating state if the HR reading or HR intensity significantly increases; an aerobic endurance state if the increased HR intensity is fixed within a zone wherein the HR intensity fluctuates between a range about +/−1 to about +/−20% of the average HR intensity of this state; and a dynamic recovery state if the HR intensity decreases about 1% to about 20% than an average HR intensity during the aerobic endurance state for a time period that is longer than that of the sprint or compensating state; and (c) displaying the real-time workload status including the sprint, the compensating, the aerobic endurance or the dynamic recovery status.

DETAILED DESCRIPTION OF THE INVENTION

Figure 1:
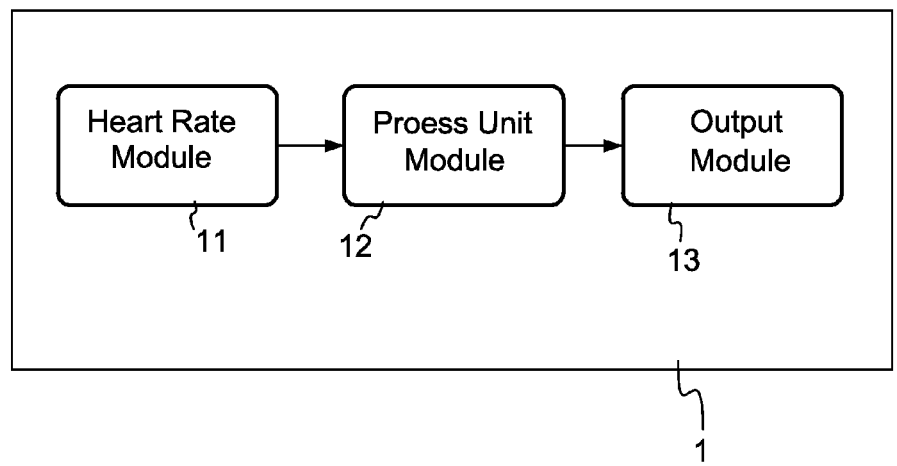
FIG. 1 is a block diagram of components of the real-time exercise coaching system according to an embodiment of the present invention.

The invention provides a real-time exercise coaching system on the basis of that the whole exercise course could be subdivided into 4 basic components: sprint (anaerobic sprint exercise or sprint speeding), aerobic endurance (balancing aerobic endurance), oxygen-compensating (compensating $O_2$ debt), and dynamic recovery. The real-time exercise coaching system of the invention enables a user to realize his/her current physiological state and change of fitness condition and then the user can further decide which action (sprint, aerobic endurance, and dynamic recovery) is to be taken next. The system of the invention instantly and continuously provides information that assesses a user's current physiological state during exercising in view of the exercise situations and the environmental conditions (such as temperature, humidity, altitude and air quality). Accordingly, immediate fitness state can be known so that over- or under-workout can be avoided and an ideal interval workout can be achieved. Also, the system of the invention has smart and personalized functions that provide dynamic and instant signals in combination with a simple interface design and easy to operate.

The present invention will now be described in detail with reference to the embodiments thereof as illustrated in the accompanying drawings. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases may not necessarily refer to the same embodiment. Further, when a particular feature, structure, or characteristic is described in connection with an embodiment, it is submitted that it is within the knowledge of persons skilled in the art to affect such feature, structure, or characteristic in connection with other embodiments whether or not explicitly described.

In one aspect, the invention provides a real-time exercise coaching system comprising:
(a) a heart rate (HR) module to acquire heart rate parameters;
(b) a process unit module to retrieve the HR parameters from the HR module to obtain a HR reading and/or a heart rate intensity (HR intensity) and determine a real-time workload status: a sprint or compensating state if the HR reading or HR intensity significantly increases; an aerobic endurance state if the increased HR intensity is fixed within a zone wherein the HR intensity fluctuates between a range about +/−1 to about +/−20% of the average HR intensity of this state; and a dynamic recovery state if the HR intensity decreases about 1% to about 20% than an average HR intensity during the aerobic endurance state for a time period that is longer than that of the sprint or compensating state; and
(c) an output module to display the real-time workload status including the sprint, the compensating, the aerobic endurance or the dynamic recovery status.

In another aspect, the invention provides a method for real-time coaching exercise, comprising (a) acquiring heart rate parameters; (b) retrieving the HR parameters from the HR module to obtain a HR reading and/or heart rate intensity (HR intensity) and determining a real-time workload status: a sprint or compensating state if the HR reading or HR intensity significantly increases; an aerobic endurance state if the increased HR intensity is fixed within a zone wherein the HR intensity fluctuates between a range about +/−1 to about +/−20% of the average HR intensity of this state; and a dynamic recovery state if the HR intensity decreases about 1% to about 20% than an average HR intensity during the aerobic endurance state for a time period that is longer than that of the sprint or compensating state; and (c) displaying the real-time workload status including the sprint, the compensating, the aerobic endurance or the dynamic recovery status.

With reference to FIG. 1, in one embodiment of the real-time exercise coaching system 1 may comprise a heart rate module 11, a process unit module 12; and an output module 13.

The heart rate (HR) module 11 is adapted to detect the heart rate parameters and transmits the resulting parameters to the process unit module 12. Heart rate parameters can be obtained by any devices known in the art. Heart rate is the number of heartbeats per unit of time, typically expressed as beats per minute (bpm). Heart rate is measured by finding the pulse of the body. A more precise device to determine the pulse involves the use of an PPG (photoplethysmograph), ECG (electrocardiograph, also abbreviated as EKG) or a heart rate monitor. In one embodiment, the HR parameters include, but are not limited to, heart rate and/or RR interval of the continuous heart rhythm. The RR interval denotes to R wave to R wave interval that is the inverse of the heart rate. The RR interval also can be detected by the PPG, ECG or heart rate monitor.

The process unit module 102 is adapted to retrieve the HR parameters from the HR module to obtain a HR reading or for determination of a heart rate intensity (HR intensity) and to determine a real-time workload status: a sprint or compensating state if the HR reading or HR intensity significantly increases; an aerobic endurance state if the increased HR intensity is fixed within a zone wherein a HR intensity fluctuates between a range about +/−1 to about +/−20% of the average HR intensity of this state; and a dynamic recovery state if the HR intensity decreases about 1% to about 20% than the average HR intensity of the aerobic endurance state for a time period that is longer than that of the sprint or compensating state. According to the invention, in the aerobic endurance state, the increased HR intensity is fixed within a zone. In the zone, the HR intensity fluctuates between a range about +/−1 to about +/−20%, about +/−1 to about +/−15%, about +/−1 to about +/−10%, about +/−1 to about +/−8%, about +/−3 to about +/−20%, about +/−3 to about +/−15%, about +/−3 to about +/−10%, about +/−3 to about +/−8% or about +/−3 to about +/−5% of the average HR intensity of this state; more preferably, the HR intensity fluctuates between a range about +/−5%. According to the invention, in an aerobic endurance state, the user can determine the time period while the HR intensity fluctuates within the zone. If the user goes on another sprint or dynamic recovery, the HR intensity would not maintain in the zone. In one embodiment, in a dynamic recovery state, the HR intensity decreases about 1% to about 20%, about 1% to about 15%, about 1% to about 10%, about 1% to about 8%, about 3% to about 20%, about 3% to about 15%, about 3% to about 10% or about 1% to about 8%; more preferably, the HR intensity decreases about 5%. According to the invention, in the dynamic recovery state, the HR intensity continuously decreases for a time period (second) that is longer than that of the sprint or compensating state; preferably, the time period is one times (more preferably, two times) longer than that of the sprint or compensating state.

The invention imitates cardiac motion and provides an advantageous assessment for workload status mainly on the basis of HR intensity (also known as percent heart rate reserve, heart rate capacity, target heart rate, or % HRR). Various equations or formulae for determining the HR intensity can be used in the invention. In one example, the HR intensity may be calculated by dividing HRmax by the predicted age compensated maximum heart rate as follows:

$$\% \, HRR = \frac{HR_{max} - \text{Resting } HR}{\text{Age compensated maximum } HR - \text{Resting } HR} * 100$$

In the equation indicated above, the maximum heart rate (HRmax) is the highest heart rate an individual can safely achieve through exercise stress, and depends on age. The resting heart rate (HRrest) of an individual may be obtained by any suitable method including, for example, a heart rate measurement taken when the activity level of the individual is sufficiently low to be considered inactive. Alternatively, the HRrest is an individual's heart rate when he/she is at rest, that is lying down but awake, and not having recently exerted themselves. The age compensated maximum heart rate can be calculated by the formula: (220-age). Other calculations of age-predicted maximal heart rate are provided by Hirofumi Tanake et al (J of Am college of Cardiology 2001: 153-6).

The heart rate variability (HRV) also can be obtained by the process unit module 102 to further assess the workload status. The heart rate variability (HRV) generally refers to the beat-to-beat fluctuations in heart rate (e.g., variation in R-R interval) that occurs as a normal physiological response (e.g., an internal response to neuronal or endocrine influence), or variations in heart rate that occur in response to external stimuli. In general, heart rate variability reflects the non-invasively autonomic nervous system activity (e.g., the sympathetic and parasympathetic influences upon the heart beat's rate and rhythm). Short-term (beat-to-beat) variability in heart rate represents fast, high-frequency (HF) changes in the heart rate. For example, changes in heart rate associated with breathing are characterized by a frequency of between about 0.15 and about 0.4 Hz (corresponding to a time constant between about 2.5 and 7 seconds). Low-frequency (LF) changes in heart rate (for example, blood pressure variations) are characterized by a frequency of between about 0.04 and about 0.15 Hz (corresponding to a time constant between about 7 and 25 seconds). Very-low-frequency (VLF) changes in heart rate are characterized by a frequency of between about 0.003 and about 0.04 Hz (0.5 to 5 minutes). Ultra-low-frequency (ULF) changes in heart rate are characterized by a frequency of between about 0.0001 and about 0.003 Hz (5 minutes to 2.75 hours). A commonly used indicator of heart rate variability is the ratio of HF power to LF power. A normalized LFP can be calculated through an equation of LF/(TP−VLF) (n.u.) and a normalized HFP can be calculated through an equation of HP/(TP−VLF) (n.u.), wherein TP is total power ($ms^2$). In one embodiment, a real-time workload status can be determined: a sprint or compensating state if a HR reading or HR intensity significantly increases while normalized LFP decreases; an aerobic endurance state if the increased HR reading is fixed within a zone wherein a HR intensity fluctuates between a range +/−1 to +/−20% of the average HR intensity of this state and LFP equals to HFP; and a dynamic recovery state if the heart intensity decreases 1% to 20% than an average HR intensity and the normalized HFP elevates during the aerobic endurance state for a time period that is two times longer than that of the sprint or compensating state.

The output module 13 is adapted to display the suggestions from the process unit module 12 including the sprint, the aerobic endurance, the compensating and the dynamic recovery statuses to coach the user's exercise. In one embodiment, a visual display can be used for displaying suggestions. For example, the suggestions displayed by the output module 103 include (a) a suggestion regarding recovery and sprint, and (b) a suggestion regarding increase and reduction of velocity. The suggestion (a) is provided for determining whether to take dynamic recovery (reduce exercise strength) or sprint (increase exercise strength or speeding). The suggestion (b) is provided for the determining whether to increase or decrease velocity so that the user can best approach the predetermined target but within the user's physiological tolerance based on a predetermined target time and physiological situation.

Figure 2:
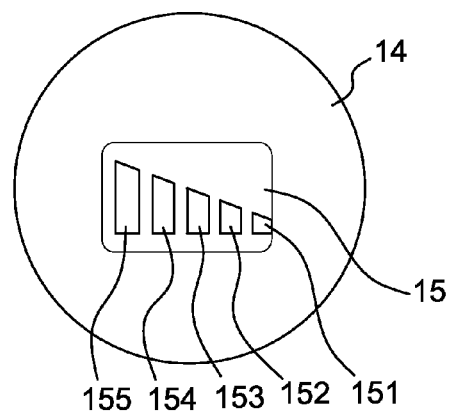
FIG. 2 is a visual display of the output module of the real-time exercise coaching system showing workload status according to an embodiment of the present invention.

FIG. 2 is a visual display 14 for the output module 13 for one embodiment of the present invention showing a color level display 15 for a real-time workload status. In the prior art, a fixed heart rate zone corresponds to a color and color changes depending on different heart rate zone, which does not take current exercise status (such as anaerobic sprint, aerobic endurance, recovery and oxygen debt compensation) and body workload status into consideration. However, in the invention, the colors varies depending on the real time workload status, so the invention can allow its user to obtain more accurate data and thus achieve one or more specific fitness or exercise goals. The numbers and types of color levels of the visual display used to display the workload status can be designed according to the objective and necessity of the manufactures. For example, the color levels can be shown with fixed colors and/or blinking colors and the numbers of the color levels may range from 1 to 20 color levels, 1 to 10 color levels, 1 to 7 color levels, or 1 to 5 color levels. For example, the workload status can be displayed with 5 color levels in combination with a fixed and/or a blinking color. For example, the color levels range from blue to red, so that from the lowest to the highest sequence are blue (B) 151, green (G) 152, yellow (Y) 153, orange (O) 154 and red (R) 155 and the blinking color of the color level is denoted with the symbol "*." In one embodiment, when the user undergoing an anaerobic sprint enters into a mainly aerobic endurance stage (with certain strength), the color elevates one level with a fixed color, so the color level display will change from B to BG, from BG to BGY, from BGY to BGYO, or from BGYO to BGYOR. In one embodiment, when the user is engaging in an anaerobic sprint or compensating extra previously banked oxygen debt, the color elevates to the next level with a blinking color, so the color level display will change from B to BG*, from BG to BGY*, from BGY to BGYO*, or from BGYO to BGYOR*. In one embodiment, when the user is in dynamic recovery, the color decreases one level with a fixed color, so the color level display will change from BG to B, from BGY to BG, from BGYO to BGY, or from BGYOR to BGYO.

In another embodiment, the visual display 14 for the output module 13 can further combine with an audio output display and/or a vibration output display. In one embodiment, when the color level showing workload status is blinking, an audio output display and/or a vibration output display can be used. The audio output display and vibration output display can be designed according to those known in the art. In one embodiment with an audio output display, a short sound represents that the color level is blinking, a long sound represents that the color level is at the upper and/or lower limit of a color zone, and a speech sound can give notifications such as "increase speed," "reduce speed," "increase number of breaths," "reduce number of breaths," "deep breath" or "drink water."

In one embodiment with a vibration output display, a short vibration (2 seconds) represents that the that the color level is blinking, a long vibration represents that the color level is at the upper and/or lower limit of a color zone, and rhyme pattern vibration can be used to assist a user to adjust his/her breath. An example of rhyme pattern is vibrating once (2 seconds) every 3 seconds. The rhyme pattern varies depending on the user's physiological situation so that the user can achieve an effective aerobic respiration.

Figure 3:
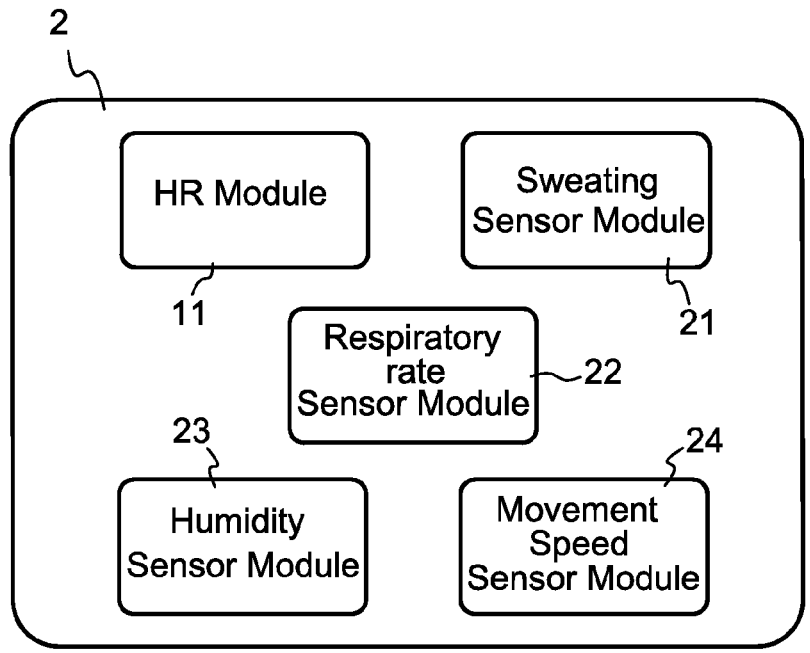
FIG. 3 is a block diagram of sensor modules contained in the integrated sensor module of the real-time exercise coaching system according to an embodiment of the present invention.

In another embodiment, with reference to FIG. 3, the real-time exercise coaching system 2 may further comprise one or more sensor module(s) selected from a group consisting of a body temperature and sweating sensor module 21, a respiratory rate sensor module 22, an environmental temperature and humidity sensor module 23, and a movement speed sensor module 24. The body temperature and sweating sensor module 21 is adapted to sense an early stage exhaustion signal by collecting information regarding monitoring body surface temperature, humidity and capillary contraction to monitor muscle exercise to determine whether the early stage exhaustion appears. Upon detecting the early stage exhaustion, an alert will be announced. The respiratory rate sensor module 22 is adapted to sense the respiration rate that is an important reference of the user's exercise state. The respiration rate in combination with other sensor information can determine whether hyperventilation appears and whether workout efficiency reduces. The respiratory rate can be used to determine whether the user needs to take a break. The environmental temperature and humidity sensor module 23 is adapted to sense the environmental temperature and humidity, which assists with setting the optimal exercise strength. The movement speed sensor module 24 is adapted to detect velocity, which can be used to understand the user's type of exercise and variability of workout efficiency during exercising, thereby allowing the module to provide suggestions for which type of exercise to engage.

The data and parameters obtained from the various above-mentioned sensor modules are transmitted to the process unit module 12. In addition to the parameters of workload status, one or more parameters regarding workout efficiency, workout intension and speed or total calorie navigation indicator can be obtained by the process unit module 12 and then the suggestions regarding workout efficiency, workout intension, and speed or total calorie navigation indicator can be displayed by the output module 13. In a further embodiment, the current heart rate can be displayed by the output module 13.

In one embodiment, according to the invention, workout efficiency exhibits the entire exercise efficiency, including heart rate from the heart rate module 11 and respiration rate from the respiratory rate sensor module 22. The user will know his/her current workout efficiency while exercising. If the exercise is in low efficiency, physiological situations of the user should be capable of recovering by adjusting the exercise strength, speed and breathing effort. In one embodiment of the invention, the workout efficiency is calculated according to the equation of (TS/DRS)+k, wherein TS refers to temporal speed denoting an average rate within 30 seconds; DRS refers to database related speed (DRS) denoting to average referring speed. The average referring speed corresponds to a lowest detected heart rate (DHR) that is the lowest heart rate within 30 seconds after starting to run the system of the invention. In one embodiment, when $1.1 \geq (TS/DRS)+k \geq 0.9$, it represents that the workout efficiency is neutral. If the "(TS/DRS)+k" value is higher than 1.1, it means that there is a higher workout efficiency. Therefore, the higher the value is, the higher the workout efficiency is. On the contrary, if the "(TS/DRS)+k" value is less than 1.1, it means that there is a lower workout efficiency. So, the lower the value is, the lower the workout efficiency is.

According to one embodiment of the invention, the workout intension is calculated based on a resting heart rate (RHR) and a maximal heart rate (MHR) for a concerned age. The RHR is variable depending on different health condition which can be automatically detected by one or more of the sensors of the invention. On the contrary, the MHR is a fixed value. Alternatively, the user can enter a value to be defined as the RHR. Since the RHR may vary according to the user's health condition on a given day, the absolute value for workout intension may also vary. The range between RHR and MHR is divided into 10 parts. The current heart rate, the RHR and the MHR are used as parameters to calculate the current workout intensity. The RHR will vary depending on the user's health state and the environmental factors (such as temperature, air pollution and altitude etc.), so the range of heart rate for each part will be adjusted based on the RHR.

According one embodiment of the invention, the speed or total calorie navigation indicator is calculated by the equation of [(total distance (total calorie)−remaining distance (remaining calorie)/remaining time]/average velocity within 5 seconds×100%.

Figure 4:
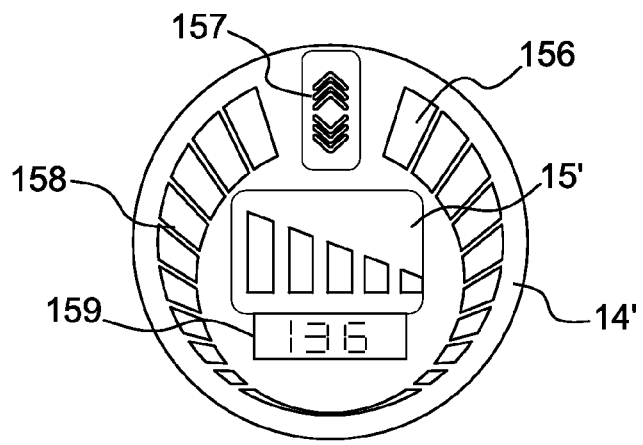
FIG. 4 is a visual display of the output module of the real-time exercise coaching system showing workload status, workload efficiency, speed or total calorie navigation indicator, workout intension and current heart status according to an embodiment of the present invention.

FIG. 4 shows an embodiment of a visual display 14' including LEDs or other suitable light sources capable of showing the workload status by a color level display 15', workout efficiency by a color display 156, speed or total calorie navigation indicator by a color display 157, workout intension by a color display 158, and current heart rate by a number display 159 to the user.

According to the invention, the workload status shown by the color level display 15' is displayed with floating 5 color levels. The color levels can be shown with fixed colors and/or blinking colors.

According to the invention, the value of workout efficiency shown by the color display 156 is calculated according to the above-mentioned equation and is divided as into +10 to neutral (N) to −10. The indicator of workout efficiency shows neutral "N" if "1.1≥the value≥0.9"; the indicator shows the "+" integer if the value>1.1; the indicator shows the "−" integer if "0.2≤the value<0.9"; and the indicator shows "Hold" if the value<0.2. All the results are displayed as color plates on the color display.

In one embodiment, the speed or total calorie navigation indicator shown by the color display 157 is a 7-band-based system. In one embodiment, the value (x) obtained from the above formula can be broken down into seven bands: 160<x, 130<x≤160, 110<x≤130, 90≤x≤110, 70<x≤90, 40<x≤70 and x≤40. The higher the value, the higher the speed (or burning calorie) is needed to achieve the goal in time.

In one embodiment, the workout intensity shown by the color display 158 shows the user's current exercise intensity. In one embodiment, the workout intensity is divided into 10 levels. The current heart rate shown by the number display 159 displays the value correlating of the user's current heart rate.

In one embodiment, the real-time exercise coaching system of the invention may be connected to a watch, a music device or a mobile phone.

The present invention has been described above by way of exemplary embodiments. Accordingly, the present invention should not be limited by any of the above-described exemplary embodiments, but should be defined only in accordance with the following claims and their equivalences.

What is claimed is:

1. A real-time exercise coaching system comprising:
(a) a heart rate (HR) module to acquire HR parameters;
(b) a process unit module to retrieve the HR parameters from the HR module to obtain a HR reading and/or heart rate intensity (HR intensity) and determine a real-time workload status: a sprint or compensating state if the HR reading or HR intensity significantly increases; an aerobic endurance state if the increased HR intensity is fixed within a zone wherein the HR intensity fluctuates between a range about +/−1 to about +/−20% of the average HR intensity of this state; and a dynamic recovery state if the HR intensity decreases about 1% to about 20% than an average HR intensity during the aerobic endurance state for a time period that is longer than that of the sprint or compensating state; and
(c) an output module to display the real-time workload status including the sprint, the compensating, the aerobic endurance or the dynamic recovery status.

2. The real-time exercise coaching system of claim 1, wherein the HR parameters comprises HR and RR interval of the continuous heart rhythm.

3. The real-time exercise coaching system of claim 1, wherein in a dynamic recovery state, the HR intensity decreases about 1% to about 20% than an average HR intensity during the aerobic endurance state for a time period that is one times longer than that of the sprint or compensating state.

4. The real-time exercise coaching system of claim 1, wherein in a dynamic recovery state, the HR intensity decreases about 1% to about 20% than an average HR intensity during the aerobic endurance state for a time period that is two times longer than that of the sprint or compensating state.

5. The real-time exercise coaching system of claim 1, wherein the output module is a visual display.

6. The real-time exercise coaching system of claim 5, wherein the visual display is shown with color levels.

7. The real-time exercise coaching system of claim 6, wherein the color levels are shown with fixed colors and/or blinking colors.

8. The real-time exercise coaching system of claim 7, wherein the color levels are 1 to 20 color levels, 1 to 10 color levels or 1 to 7 color levels.

9. The real-time exercise coaching system of claim 7, wherein the color levels are 1 to 5 color levels.

10. The real-time exercise coaching system of claim 7, wherein the color levels are 5 color levels.

11. The real-time exercise coaching system of claim 10, wherein the 5 color levels from the lowest to the highest level are sequenced as blue (B), green (G), yellow (Y), orange (O) and red (R) and the blinking color of the color level is denoted with the symbol "*."

12. The real-time exercise coaching system of claim 11, wherein when the user undergoing an anaerobic sprint enters into a mainly aerobic endurance stage, the color elevates to the next level with a fixed color, displaying from B to BG, from BG to BGY, from BGY to BGYO, or from BGYO to BGYOR; when the user is engaging in an anaerobic sprint or compensating extra previously banked oxygen debt, the color elevates to the next level with a blinking color, displaying from B to BG*, from BG to BGY*, from BGY to BGYO*, or from BGYO to BGYOR*; when the user is in dynamic recovery, the color decreases down one level with a fixed color, displaying from BG to B, from BGY to BG, from BGYO to BGY, or from BGYOR to BGYO.

13. The real-time exercise coaching system of claim 1, wherein the visual display of the output module can be further combined with an audio output display and/or a vibration output display.

14. The real-time exercise coaching system of claim 1, which further comprises one or more sensor module selected from a group consisting of a body temperature and sweating sensor module, a respiratory rate sensor module, an environmental temperature and humidity sensor module, and a movement speed sensor module.

15. The real-time exercise coaching system of claim 14, wherein one or more of workout efficiency, workout intension, speed and total calorie navigation indicator can be further obtained by the process unit module and then the suggestions regarding workout efficiency, workout intension, speed or total calorie navigation indicator and optional current heart rate can be displayed by the output module.

16. The real-time exercise coaching system of claim 15, wherein the workout efficiency is calculated according to the equation of (TS/DRS)+k, wherein TS refers to temporal speed denoting an average rate within 30 seconds; DRS refers to database related speed (DRS) denoting to average referring speed that corresponds to a lowest detected heart rate (DHR) representing the lowest heart rate within 30 seconds after starting to run the system.

17. The real-time exercise coaching system of claim 16, wherein 1.1 (TS/DRS)+k≥0.9 represents that the workout efficiency is neutral; when the value "(TS/DRS)+k" higher than 1.1, it means that there is a higher workout efficiency; and when the value "(TS/DRS)+k" is less than 1.1, it means that there is a lower workout efficiency.

18. The real-time exercise coaching system of claim 15 wherein the workout intension is calculated based on a resting heart rate (RHR) and a maximal heart rate (MHR) for a concerned age, where the RHR is variable depending on different health condition which can be automatically detected by one or more sensors of the invention and where the MHR is a fixed value.

19. The real-time exercise coaching system of claim 15, wherein the speed or total calorie navigation indicator is calculated by the equation of [(total distance (total calorie)− remaining distance (remaining calorie)/remaining time]/average velocity within 5 seconds×100%.

20. The real-time exercise coaching system of claim 15, wherein the visual display includes LEDs or other suitable light sources capable of providing information of the workload status, workout efficiency, workout intension, speed or total calorie navigation and optionally current heart rate to the user.

21. The real-time exercise coaching system of claim 20, wherein the workload status is displayed with 5 color levels with fixed colors and/or blinking colors.

22. The real-time exercise coaching system of claim 20, wherein an indicator of the workout efficiency shows neutral "N" if "1.1≥the value≥0.9"; the indicator shows the "+" integer if the value>1.1; the indicator shows the "−" integer if "0.2≤the value<0.9"; and the indicator shows "Hold" if the value<0.2.

23. The real-time exercise coaching system of claim 20, wherein the speed or total calorie navigation indicator is calculated by the equation of [(total distance (total calorie)−remaining distance (remaining calorie)/remaining time]/average velocity within 5 seconds×100% and the value (x) obtained from the above equation can be broken down into seven bands: 160<x, 130<x≤160, 110<x≤130, 90≤x≤110, 70<x≤90, 40<x≤70 and x≤40.

24. The real-time exercise coaching system of claim 20, wherein the workout intensity is divided into 10 levels.

25. The real-time exercise coaching system of claim 1, which is connected to a watch, a music device or a mobile phone.

26. A method of real-time coaching exercise, comprising (a) acquiring HR parameters; (b) retrieving the HR parameters from the HR module to obtain a HR reading or heart rate intensity (HR intensity) and determining a real-time workload status: a sprint or compensating state if the HR reading or HR intensity significantly increases; an aerobic endurance state if the increased HR intensity is fixed within a zone wherein the HR intensity fluctuates between a range about +/−1 to about +/−20% of the average HR intensity of this state; and a dynamic recovery state if the HR intensity decreases about 1% to about 20% than an average HR intensity during the aerobic endurance state for a time period that is longer than that of the sprint or compensating state; and (c) displaying the real-time workload status including the sprint, the compensating, the aerobic endurance or the dynamic recovery status.

\* \* \* \* \*